United States Patent [19]
Weissman et al.

[11] Patent Number: 6,010,850
[45] Date of Patent: Jan. 4, 2000

[54] ANALYSIS OF GENE EXPRESSION BY DISPLAY OF 3'-END RESTRICTION FRAGMENTS OF CDNAS

[75] Inventors: Sherman M. Weissman, New Haven, Conn.; Yatindra Prashar, Columbia, Md.

[73] Assignee: Yale University, New Haven, Conn.

[21] Appl. No.: 08/688,514

[22] Filed: Jul. 30, 1996

Related U.S. Application Data

[63] Continuation-in-part of application No. 08/510,032, Aug. 1, 1995, Pat. No. 5,712,126.

[51] Int. Cl.[7] ............................... C12Q 1/68; C12P 19/34
[52] U.S. Cl. ................................................ 435/6; 435/91.2
[58] Field of Search .............................. 435/6, 91.2, 91.1, 435/91.52, 91.5; 536/24.2, 24.33

[56] References Cited

U.S. PATENT DOCUMENTS 5,712,126   1/1998   Weissman et al. ..................... 435/91.2

FOREIGN PATENT DOCUMENTS

WO94/01582   1/1994   WIPO .............................. C12Q 1/68

OTHER PUBLICATIONS

Liang et al. (1994) Nucleic Acids Research 22:5763–4.
Zeng et al. (1994) Nucleic Acids Research 22:4381–5.
Cecchini et al. (1993) Nucleic Acids Research 21:5742–7.
Duguid and Dinauer (1990) Nucleic Acids Research 9:2789–92.
Liang et al. (1993) Nucleic aCids Research 21:3269–75.
Wang and Brown (1991) Proc. Natl. Acad. Sci. USA 88:11505–9.
Lisitsyn et al. (1993) Science 259:946–51.
Navarro et al. (1996) J. Virol. Methods 56:59–66.
Diachenko et al. (1996) Biochemical and Biophysical Research Communications 219:824–8.
Kato (1995) Nucleic Acids Research 23:3685–90.
Kato (1996) Nucleic Acids Research 24:394–5.
Chenchik et al. (1996) BioTechniques 21:526–34.
Straus et al. Genomic substraction for cloning DNA corresponding to deletion mutations Proc. Natl. Acad. Sci. USA vol. 87, pp. 1889–1893, 1990.

*Primary Examiner*—Kenneth R. Horlick
*Attorney, Agent, or Firm*—Foley & Lardner

[57] ABSTRACT

The present invention is directed to an approach to study changes in gene expression by the selective PCR amplification and display of 3'-end restriction fragments of double stranded cDNAs.

13 Claims, 10 Drawing Sheets

| | | | | | |
|---|---|---|---|---|---|
| 1 |  | TA1 | 8 |  | JkA6 |
| 2 |  | JkA1 | 9 |  | JkA7 |
| 3 |  | JkA2 | 10 |  | JkA8 |
| 4 |  | JkA3 | 11 |  | JkA9 |
| 5 |  | JkA4 | 12 |  | JkA10 |
| 6 |  | JkA5 | 13 |  | JkA11 |
| 7 |  | } JkR1 | 14 |  | IL-2 |
| 7(a) |  | | 15 |  | β-Actin |

6,010,850

ANALYSIS OF GENE EXPRESSION BY DISPLAY OF 3'-END RESTRICTION FRAGMENTS OF CDNAS

This is a Continuation in Part of our earlier filed U.S. patent application Ser. No. 08/510,032, filed Aug. 1st 1995 U.S. Pat. No. 5,712,126.

STATEMENT OF GOVERNMENT INTEREST

This invention was made, at least in part, with government support under grant number CA-42556-10, awarded by the Department of Health and Human Services. As such, the government may have certain rights in the invention.

BACKGROUND OF THE INVENTION

The identification of genes associated with development, differentiation, disease states, and response to cellular environment is an important step for advanced understanding of these phenomena. Specifically, effective methods for conducting genetic analysis are needed to identify and isolate those genes that are differentially expressed in various cells or under altered cell environments.

Early methods developed to identify and clone such genes were primarily based on the principle of differential or subtractive hybridization [see Proc. Natl. Acad. Sci. USA 88:2825 (1991); Nature 308:149 (1984); Proc. Natl. Acad. Sci. 84:1609 (1987); and Mol. Cell Biol. 9:1041 (1989)]. Despite the usefulness of these methods, they can only analyze a fraction of the overall changes in gene expression, require large amounts of ribonucleic acid (RNA), and are lengthy and labor intensive.

Recently, Liang and Pardee [see Science 257:967 (1992)] developed a gel-based technique that facilitates a rapid and extensive analysis of differentially-expressed messenger RNA (mRNAs). Very briefly, this technique was directed toward the identification of differentially expressed genes among the approximately 15,000 individual mRNA species in a pair of mammalian cell populations, and then recovering their complementary deoxyribonucleic acid (cDNA) and genomic clones. The general strategy was to amplify partial complementary cDNA sequences from subsets of mRNAs by reverse transcription and the polymerase chain reaction. These short sequences would then be displayed on a sequencing gel. In this technique, pairs of 10-mer primers were selected so that each would amplify cDNA from about 50 to 100 mRNAs, because this number was optimal under this technique for display on the gel [Science 257:967 (1992); and see also U.S. Pat. No. 5,262,311, the disclosure of which is incorporated in toto herein].

Several groups have successfully employed the Liang and Pardee technique to identify differentially expressed genes [see Trends Genet. 11:242 (1995); Curr. Opinion Immunol. 7:274 (1994); and Nucleic Acids Res. 19:4009 (1994)]. However, limitations associated with this technique—limitations such as the lack of quantitative correlation with mRNA abundances, a significant incidence (up to 80%) of false positive signals, variable reproducibility of the display patterns, multiple sequences migrating in the gel to produce a single signal, and under-representation and redundancy of mRNA signals [see Trends Genet. 11:242 (1995); Nucleic Acids Res. 22:5763 (1994); and FEBS Let. 351:231 (1994)]—have made it difficult to fully and correctly evaluate differential gene expression. More importantly, the size of bands is not always readily predictable from the mRNA sequence.

Amplification of cDNAs at the low primer annealing temperature of 40° to 42° C., a non-stringent PCR condition, as used in the Liang and Pardee technique is now considered to be a major limitation of current gel display protocols [see Trends Genet. 11:242 (1995); Biotechniques 18:842 (1995); and Biochem. Biophy. Res. Commun. 199:564 (1994)]. Adaptations of the original protocol have been reported in order to overcome some of these limitations, such as the use of one base anchored oligo-dT primer for increased representation of mRNAs [see Nucl. Acid. Res. 22:5763 (1994)], and the use of long composite primers to achieve reproducible patterns under more stringent PCR conditions [see Nucl. Acid. Res. 22:5763 (1994); and FEBS Let. 351:231 (1994)]. However, all these modifications continue to involve annealing of arbitrary primers at approximately the first few rounds of amplification 40° to 42° C.

SUMMARY OF THE INVENTION

According to the present invention, an alternative approach is provided for cDNA display on gels to those described by Liang and Pardee or to those described by subtractive or differential hybridization techniques. Display patterns are generated when restriction enzyme digested double stranded (ds) cDNA is ligated to an adapter that mediates selective PCR amplification of 3'-end fragments of cDNAs under high stringency PCR conditions, instead of non-stringent arbitrary cDNA amplification as taught by Liang and Pardee.

In the present invention, a diversity of patterns is generated by choosing different sets of restriction enzymes and anchored oligo-dT primers. Since all cDNAs in a sample acquire a common heel (a Nheelm is a DNA sequence not presented in the DNA being synthesized) from the oligo-dT primer during synthesis, most cDNA molecules in a subset (determined by the anchor nucleotides of the oligo-dt) can be displayed by choosing a combination of restriction enzymes while minimizing under-representation or redundant-representation of mRNAs. This approach provides near-quantitative information about the levels of gene expression, can resolve hidden differences in the display gel, produces a single band for each mRNA species, and produces bands of predictable size for known gene sequences. Most importantly, the method according to the present invention produces consistently reproducible display patterns.

Accordingly, one aspect of the present invention is to describe an assay method that, when compared to presently used methods for such assays, achieves a decrease in false positive signals; provides a reproducible technique for identifying and displaying gel patterns of DNA; provides a means for distinguishing multiple sequence signals for sequences that co-migrate to a single band in conventional techniques; avoids under representation and redundancy of RNA; and utilizes stringent conditions for PCR annealing.

This and other aspects of the present invention will become clearly understood by reference to the following figures, examples, and description of the invention.

Interestingly enough, during the making of the present invention, RNA expression during early T-cell activation, an extensively studied phenomenon associated with the induction of a large number of genes within a relatively short period of time [see Annu. Rev. Immunol. 8:421 (1990); and Curr. Opinion Immunol. 7:327 (1995)], was studied as the test system. Curiously, there is a limited description of genes that are down-regulated upon T-cell activation [see Nucleic Acids Res. 19:4655 (1991); and Proc. Natl. Acad. Sci. USA 90:10260 (1993)] and the present approach offered a convenient method for looking for such products.

A scheme for the 3'-end restriction fragment display of cDNAs according to the present invention may be described by a general 5-step or more specific 7-step process.

In the general 5-step scheme for the method according to the present invention, step 1 involves the use of a two base anchored oligo-dT primer with a heal for first strand cDNA synthesis from total RNA using reverse transcriptase. In this step, all reagents of the reaction except reverse transcriptase are mixed, overlayered with mineral oil and heated at 65° C. for 7 minutes to allow opening of any secondary structures formed in the mRNA. Thereafter, the temperature is lowered to 50° C. for 7 minutes to allow the anchored oligo-dT primer to anneal to the mRNAs. At this stage, 2 μl of Supercript II reverse transcriptase (Gibco BRL) is added to the reaction mixture, mixed by pipetting, and the reaction is carried out at 50° C. for 1 hour.

Figure 1:
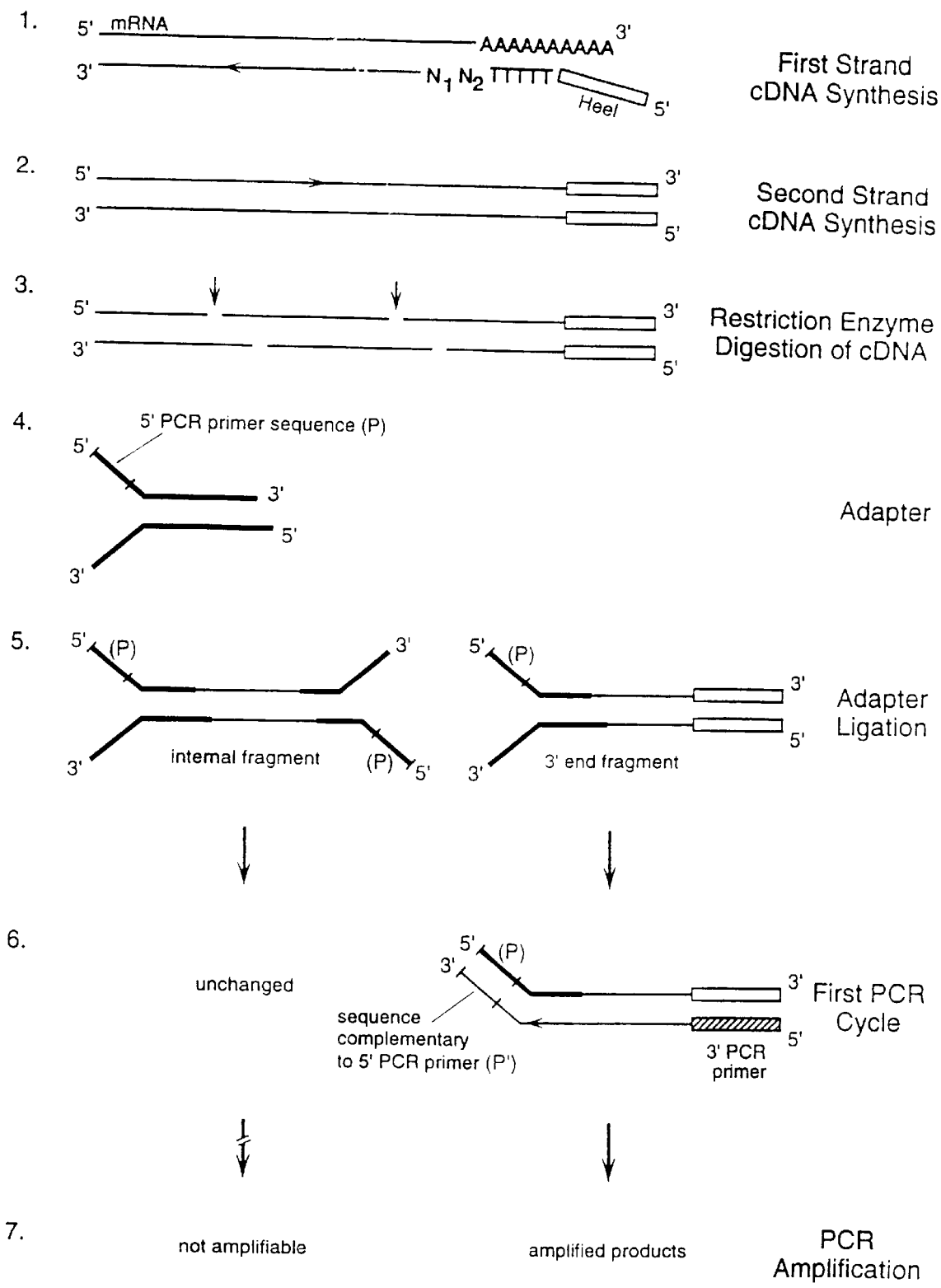
FIG. 1 is an outline schematic of the method for 3'-end cDNA amplification according to the present invention.

In the second step, the reaction mixture from the previous step is used as the substrate for the second strand cDNA synthesis by the Gubler-Hoffman method at 16° C. for 2 hours. All cDNA molecules synthesized thus acquire a common 3'-heel as shown in FIG. 1. Synthesized double stranded cDNAs are recovered by phenol-chloroform extraction of the reaction mixture, precipitated by ammonium acetate and ethyl alcohol, and dissolved in water. In the third step, cDNAs from step 2 are digested with a restriction enzyme.

In the fourth step, the restriction enzyme digested cDNAs are ligated to a "Y"-shaped adapter as shown in FIG. 1. This adapter has an overhang on its 3'-end for ligation, and on the 5'-end it has a stretch of non-complementary sequence on the opposite strands giving rise to its "Y" shape. As a result of ligation, the 3'-end restriction fragments will have adapter only on their 5'-end, while internal restriction fragments of the cDNAs will have the adapter ligated to their 5'- and 3'-ends.

In the fifth step, the 3'-end restriction fragments of the cDNAs ligated to the Y-shaped adapter are selectively amplified. The 5' PCR primer used is made from the Y region of the adapter which does not have the complementary sequence on the opposite strand and, therefore, cannot anneal to the adapter itself. The upstream fragments of digested cDNA with adapter ligated on both ends or only one end in the 5'-terminal piece will, therefore, not be PCR-amplified. However, the 3' PCR primer (made from the 3'-end heel sequence) anneals to the heel of the 3'-end fragments of cDNA during the first PCR cycle, and extends DNA synthesis into the Y region of the ligated adapter, thus synthesizing complementary sequences to which the 5' PCR primer can now anneal. The two PCR primers can then selectively amplify the 3'-end fragments of the cDNA under stringent conditions.

The more specifically described general 7-step scheme for the method according to the present invention is also shown in FIG. 1. A two base anchored, oligo-dT primer with a 3' heel is used for first strand synthesis by Gubler-Hoffman method [see Gene 25:263 (1983)] All cDNA molecules thus acquire a common 3' heel. This cDNA is digested with a restriction enzyme and ligated to a Y-shaped adapter similar in principle to the bubble adapter [see Nucleic Acids Res. 18:2887 (1990)]. The "Y" adapter is synthesized with an overhang on its 3'-end for ligation, and on its 5'-end it has a stretch of non-complementary sequence on the opposite strands that provides for its 'Y' shape. The 5' PCR primer is synthesized from this Y region and cannot anneal to the adapter itself. The upstream fragments of digested cDNA with adapter ligated on both the ends, or only one end in the 5' terminal piece will, therefore, not be PCR amplified. However, the 3' primer anneals to the heel of the 3'-end fragments of cDNA during the first PCR cycle and extends DNA synthesis into the Y region of the ligated adapter, thus synthesizing complementary sequences to which the 5' PCR primer can now anneal. The two PCR primers can then selectively amplify the 3'-end fragments of the cDNA under stringent PCR conditions.

More specifically FIG. 1 presents a method whereby a two base anchored oligo-dT primer with an added heel is used for first strand cDNA synthesis from total RNA using reverse transcriptase (step 1). This is followed by a second strand synthesis using the Gubler-Hoffman method (step 2). All cDNA molecules synthesized according to these two steps will thus acquire a common 3' heel. Next the cDNA is digested (step 3) with a selected restriction enzyme (at this point restriction enzymes that produce either blunt ends or overlapping ends may be used, however, in the following examples the enzyme BstY1 is depicted which produced overhanging ends) and ligated to a previously synthesized Y-shaped adapter (step 4). The adapter has an overhang on its 3'-end for ligation, and on its 5'-end has a stretch of non-complementary sequences that provide for its shape. The 5' PCR primer is made from this Y region (step 4) and thus cannot anneal to the adapter itself. The upstream fragments of digested cDNA with adapter ligated on both the ends (step 5) or only one end in the 5' terminal piece will, therefore, not be PCR amplified. However, the 3' primer will anneal to the heel of the 3'-end fragments of cDNA (step 5) during the first PCR cycle and extend DNA synthesis into the Y region of the ligated adapter, thereby synthesizing complementary sequences to which the 5' PCR primer can now anneal (step 6). The two PCR primers can then selectively amplify the 3'-end fragments of the cDNA under stringent conditions (step 7).

Alternatively, oligo-dU primers may be used in lieu of the oligo-dT primers for first strand cDNA synthesis in step 1. The binding of oligo-dU to the polyA stretch is known to be weaker when compared to the binding by oligo-dT. Hence, the use of oligo-dU primers for first strand cDNA synthesis should minimize the annealing of the oligo-dU to any shorter internal polyA stretches present in the mRNA polymer. The preliminary results from a set of experiments where oligo-dU was used showed typical display patterns with a known sample of RNA. These patterns were similar to those obtained by using oligo-dT, however, when using oligo-dU, the chances of the primer starting cDNA synthesis form internal polyA stretches in the mRNA polymer are minimized.

We have also discovered that PCR primers that were purified over gel electrophoresis or by HPLC will give better display patterns than unpurified primers. During oligonucleotide synthesis, a significant fraction of shorter oligonucleotides that form as a result of failed synthesis cycles are accumulated along with the complete oligonucleotide. These shorter sequences are known in the art as 'failure sequences', and although a small fraction of the original oligonucleotide can still participate in amplification during PCR, by making these smaller than normal amplified products, a product is obtained that contributes to the smear in between the bands. Accordingly, it is preferred and highly recommended that the primers used in the invention described herein be purified to lessen the number of failure sequences.

Each six base cutter restriction enzyme cuts approximately 8% of the cDNAs at positions between 50 and 400 bases from the polyA tract, so that more than 12 six base cutters will be needed to approach complete representation of cDNAs, each being used with several different anchored oligo-dT primers. Also, we estimate that at best, about 100–150 discrete bands can be detected in a single gel lane. Therefore, at least 100 lanes will need to be run under different conditions to study the overall pattern of gene expression in any single cell type. By using 30 restriction enzymes to cut a cell-derived cDNA, it has been possible to cover, according to the present invention, approximately 97% of the cDNAs from a single cell.

A major advantage of the present approach is that the size of a known cDNA product and hence its position on the display gel is predictable. lnterleukin-2 (IL-2) is a well studied cytokine expressed only in activated and not resting T-cells [see Annul. Rev. Immunol. 8:421 (1990)] and should be displayed as band of predictable size. To confirm this and to test the ability of the method to display differences, cDNA from resting and activated human peripheral blood T-lymphocyte RNA were made using oligo-dT primer with a heel and 3' anchor residues TA complementary to the AT dinucleotide in the IL-2 mRNA sequence immediately preceding the polyA tail. Restriction digestion with BstY1 should produce, and did when tested, a 146 bp 3'-end fragment of IL-2 cDNA [see Natl. Acad. Sci. USA 81:2541 (1984)]. When added to the sizes of the 3' oligo dT and 5' adapter, this should, and did, produce a band of 209 bp on the display gel. A distinct band of the predicted size was produced in activated (FIG. 2, lane 2) but not in the resting (FIG. 2, lane 1) T-cell sample on display of BstY1 cut cDNA DNA sequence analysis of this fragment confirmed the presence of the 5' adapter followed by a BstY1 site, IL-2 3'-end sequences, the polyadenylation signal AATAAAA (SEQ. NO. 1), the downstream oligo-A tract and the heel primer.

EXAMPLE 1

Conditions for growth and activation of Jurkat (Jurkat T-cells grow rapidly in culture, can be synchronized by serum starvation, and can be stimulated to produce interleukin-2, an early event in the differentiation of peripheral blood T-cells in vivo; as a result they have become a recognized model system for the comprehensive identification and cloning of all DNA sites that are specifically recognized by protein factors present in these cells; the use of Jurkat T-cells as a model is well accepted, and the findings using this test system may readily be extrapolated to other test systems using other cell types; in short, it is scientifically reasonable to accept Jurkat T-cells as a standard for the comprehensive identification and cloning of all DNA sites that are specifically recognized by protein factors present in these cells, and this may be extrapolated for the comprehensive identification and cloning of all DNA sites that are specifically recognized by protein factors present in other cell types) and peripheral blood T-cells, respectively, have been previously described [see Proc. Natl. Acad. Sci. USA 90:10260 (1993); and J. Exp. Med. 174:1259 (1991), the disclosures of which are incorporated herein in toto]. Total cellular RNA was prepared from untreated (JO) and 4 hour Phorbol 12-Myristate 13-Acetate (PMA) plus Phytohemagglutinin (PHA) activated Jurkat cells (JTP) using RNAzol (Bibco-BRL). Synthesis of cDNA was performed according to the manufacturer's instructions (Gibco-BRL kit for cDNA synthesis). The reaction mixture for first strand synthesis included, 10 µg total RNA, 2 pmols of one of the following three nucleotide anchored heeled oligo-dT primers (wherein T18 refers to a string of 18 thymine-based nucleotides):

RP5.0 CTCTCAAGGA TCTTACCGCT $T_{18}$AT 40 (SEQ. NO. 2);

RP6.0 TAATACCGCG CCACATAGCA $T_{18}$CG 40 (SEQ. NO. 3); or

RP9.2 CAGGGTAGAC GACGCTACGC $T_{18}$GA 40 (SEQ. NO. 4)

along with other conventional reagents for the first strand synthesis reaction except reverse transcriptase. In these three sequences, the "true" heel is to be considered to be the first 20 nucleotides (that is the molecule without the $T_{18}$ AT, $T_{18}$CG, or $T_{18}$GA portion. Thus, the "true" heels are

CTCTCMGGATCTTACCGCT 20 (SEQ. NO. 10);

TAATACCGCG CCACATAGCA 20 (SEQ. NO. 11); and

CAGGGTAGAC GACGCTACGC 20 (SEQ. NO. 12).

The reaction mixture was layered with mineral oil, incubated at 65° C. for 7 minutes followed by 50° C. for another 7 minutes. At this stage 2 µl of Superscript reverse trascriptase (200 u/µl, Gibco-BRL) was added quickly, mixed, and the reaction continued for an additional hour at 50° C. Second strand synthesis was performed at 16° C. for 2 hours. At the end of the reaction the cDNAs were precipitated with ethanol and the yield (approximately 100 ng) of cDNA was calculated.

The adapter of the following A1 and A2 nucleotide molecules was next synthesized with the following sequences:

A1 TAGCGTCCGG CGCAGCGACGG CCAG 25 (SEQ. NO. 5); and

A2 GATCCTGGCCGTCGGCTGTCTGTCGGCGC 29 (SEQ. NO. 6)

One µg of oligonucleotide A1 was first kinased at the 5'-end in a final reaction volume of 10 µl using T4 polynucleotide kinase (PNK) with conventional techniques. After phosphorylation, PNK was heat denatured, and 1 µg of the oligo A2 was added along with 10×annealing buffer (1M NaCl, 100 mM Tris, HCl pH 8.0, and 10 mM EDTA pH 8.0) in a final working volume of 20 µl. This mixture was then heated at 65° C. for 10 minutes, followed by slow cooling to room temperature for 30 minutes. This results in the formation of the "Y" adapter at a final concentration of 100 ng/µl. About 20 ng of the cDNA was digested with 4 units of Bgl II in a 10 µl reaction for 30 minutes. Two µl (~4 ng digested cDNA) of this reaction mix was then used for ligation to 100 ng (~50 fold) of the Y-shaped adapter. The ligation was carried out for 16 hrs at 15° C. in a final volume of 5 µl (2 µl digested cDNA, 1 µl adapter, and 2 µl of a solution containing 5 µl 10 mM ATP, 5 µl 10×ligation buffer, and 10 µl (4 units) of T4 DNA ligase). Following ligation, the reaction mixture was diluted to a final volume of 80 µl (adapter ligated cDNA conc. ~50 µg/µl) and heated at 65° C. for 10 minutes to denature T4 DNA ligase, and 2 µl aliquots (with ~100 pg cDNA) were used for PCR.

The following sets of primers were used for PCR amplification of the adapter ligated 3'-end cDNAs. The RP5.0, RP6.0 or RP9.2 primers were used as the 3' primer, while the following:

A1.1 TAGCGTCCGGCGCAGCGAC 19 (SEQ. NO. 7) served as the 5' primer. In order to detect the PCR products on the display gel, oligo A1.1 was 5'-end labeled for 30 minutes in a final reaction volume of 20 µl containing 24 pmoles of this oligo, 10 units of PNK, and 48 pmoles, i.e., 15 µl of $\gamma^{32}$P ATP (Amersham). PNK was heat denatured at 65° C. for 20 minutes and the labelled oligo was mixed with 60 µl of 2 µM of unlabelled oligo 1.1 (at a 1:4 dilution, final oligo concentration of ~2 µM). The PCR reaction mixture (20 µl) consisted of 2 µl (~100 pg) of the template, 2 µl of 10×PCR buffer (100 mM Tris-HCl and 500 mM KCl), 2 µl of 15 mM MgCl$_2$ to yield 1.5 mM final Mg$^{+2}$ concentration that is optimum for the reaction, 200 µM of dNTPs, 200 nM each of 5' and 3' PCR primers, and 1 unit of Amplitaq. Primers and dNTPs were added after preheating the reaction mixture containing the remainder of the components at 85° C. This "hot start" PCR was done to avoid artefactual amplification arising out of arbitrary annealing of PCR primers at lower temperature during transition from room temperature to 94° C. in the first PCR cycle. PCR consisted of 28 to 30 cycles at the stringent conditions of 94° C. for 30 seconds, 56° C. for 2 minutes, and 72° C. for 30 seconds. A higher number of cycles resulted in smeared gel patterns.

Alternatively, the PCR amplification conditions may be modified in order to achieve an even higher stringency for primer annealing by using stretch-PCR conditions. For this purpose, we have routinely used radio-labelled primer A1 (i.e., Sequence No. 5) as the 5' PCR primer instead of the primer A1.1 described above. The PCR conditions for this stretch-PCR procedure are 94° C. for 30 seconds, 68° C. for 2 minutes, and 45 seconds for 30 cycles. The results obtained by using this protocol showed improved sharpness of the bands on the display gels.

PCR products (2.5 µl) were analyzed on a 6% polyacrylamide sequencing gel. For double or multiple digestion following adapter ligation, 13.2 µl of the ligated cDNA sample was digested with secondary restriction enzymes in a final volume of 20 µl. From this solution, 3 µl was used as the template for PCR. This template volume of 3 µl carried ~100 pg of the cDNA and 10 mM MaCl$_2$ (from the 10×enzyme buffer) which diluted to the optimum of 1.5 mM in the final PCR volume of 20 µl. Since any Mg$^{+2}$ comes from the restriction enzyme buffer, it was not included in the reaction mixture when amplifying secondarily-cut cDNA.

In both cases, i.e., with cutting by a single or by multiple restriction enzymes, bands were extracted from the display gels, reamplified using the 5' and 3' primers, and subcloned into pCRscript with high efficiency using the PCR script cloning kit (Stratagene) and following the manufacturer's instructions. Resulting plasmids were sequenced by cycle sequencing on an Applied Biosystems automated sequencer.

An improvement in this protocol may occur if $^{33}$P is substituted as the radio-labelling isotope rather than $^{32}$P as described above. The isotope $^{33}$P emits weak beta particles and has a longer half-life than $^{32}$P. When the use of $^{33}$P was tested for labelling the PCR primers in lieu of 32P, the resulting display patterns showed very sharp bands as compared to their $^{32}$P counterparts. Based upon these series of comparisons, $^{33}$P labelling should allow a better resolution of finer bands that would normally be hidden or not discernible as a result of smudging when $^{32}$P is used.

Figure 2:
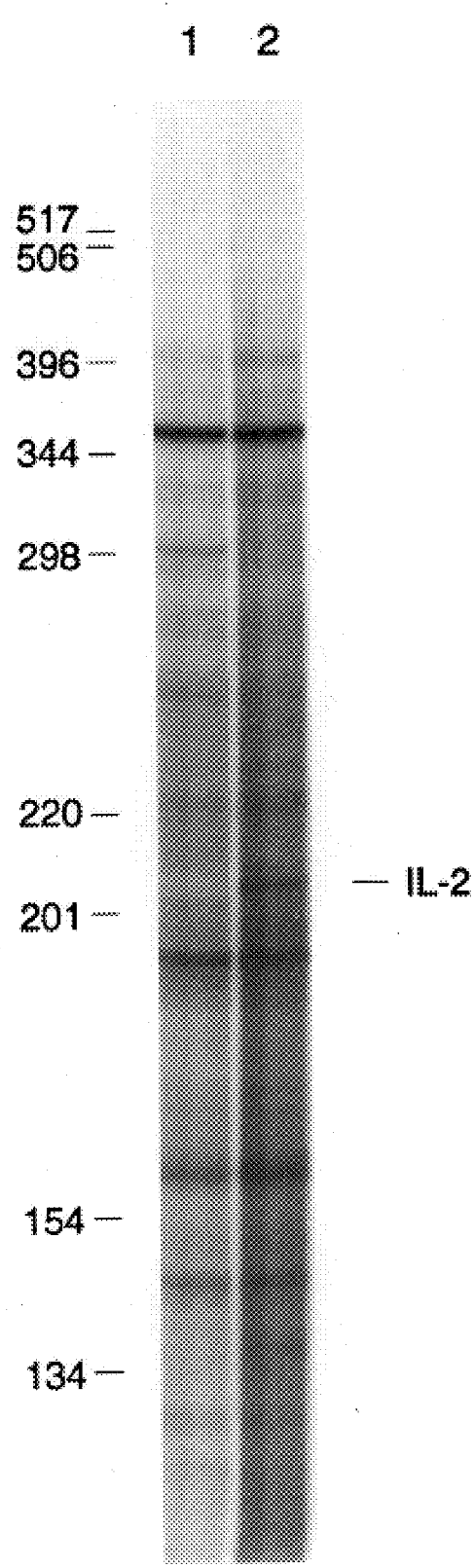
FIG. 2 is a photomicrograph demonstrating the predictability of the band size of known cDNAs on the display gel according to the present invention.

As shown in FIG. 2, the display of BstY1 digested cDNA prepared from resting and activated T-cells produced the predicted 209 nucleotide band corresponding to IL-2 mRNA 3' end sequence in activated T-cells (lane 2), but not in resting T-cells (lane 1). This is because the IL-2 gene will express the corresponding mRNA in the activated, but not in the resting, T-cells.

The total cDNA for the 209 nucleotide sequence is:

```
TAGCGTCCGG CGCAGCGACG GCCAGGATCT TTTATGATTC TTTTTGTAAG  50 (SEQ. NO. 8)

CCCTAGGGGC TCTAAAATGG TTTCACTTAT TTATCCCAAA ATATTTATTA  100

TTATGTTGAA TGTTAAATAT AGTATCTATG TAGATTGGTT AGTAAAACTA  150

TTTAATAAAT TTGATAAATA TTTTTTTTTT TTTTTTTTTT CGCCATTCTA  200

GGAACTCTC                                             209
```

In this sequence, nucleotides 1 to 25 correspond to A1, nucleotides 26 to 171 correspond to the 146 nucleotide sequence of IL-2 as reported in the literature, nucleotides 172 to 209 correspond to the nucleotides of RP5 beginning with the T18 designation.

After extracting the band from the gel it was confirmed to be IL-2 by sequencing. Before PCR amplification, the adapter ligated cDNA was recut with Alu1, Rsa1 and Msp1 since, without recutting, smeary patterns resulted as BstY1 is a frequently cutting restriction enzyme.

Figure 3:
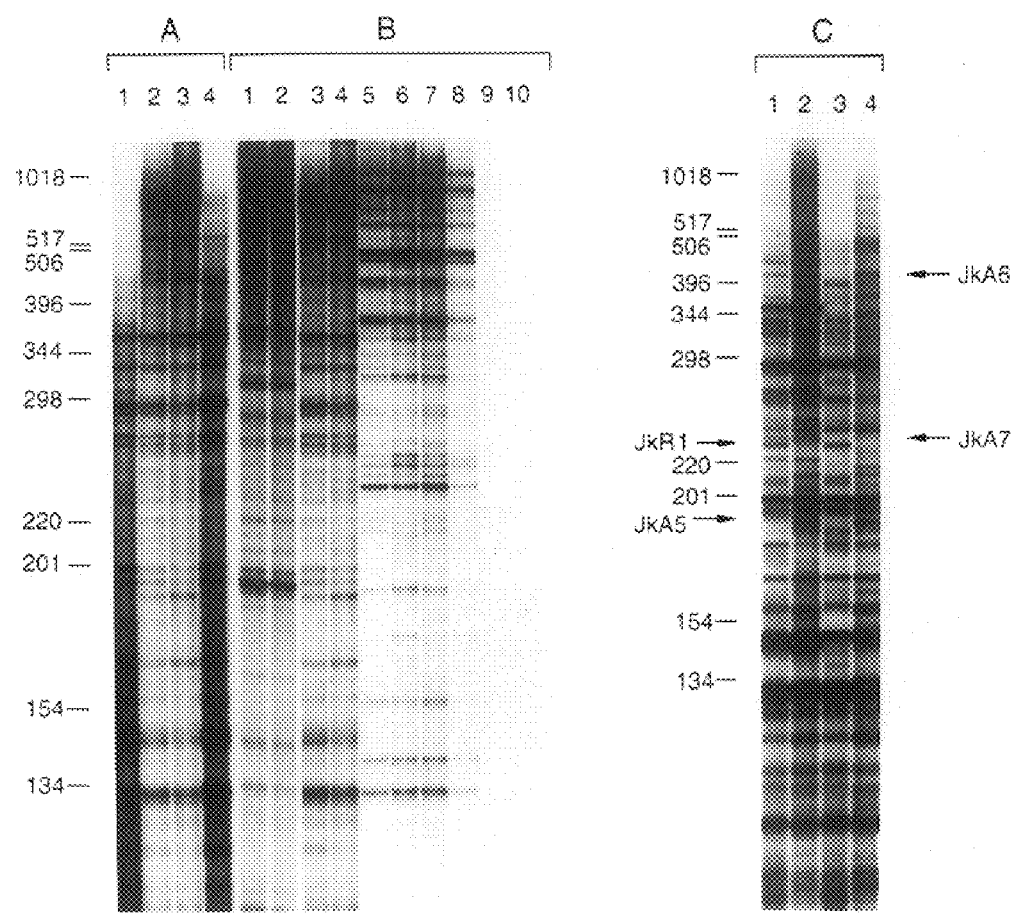
FIG. 3 is a photomicrograph demonstrating the reproducibility patterns and their diversity generated by different restriction enzymes and anchors in oligo-dT primers with heel according to the present invention.

RNA from resting and 4 hour activated Jurkat cells was next compared and displayed in FIG. 3 which, shows the reproducibility of display patterns and their diversity generated by different restriction enzymes and anchors in oligo-dT primers with heel.

FIG. 3 depicts three different panels (A, B and C). In panel A, lanes 1 and 2 are the same experiment, run at different times, using resting cells; lanes 3 and 4 are the same experiment, run at different times, using activated cells.

In both panels B and C of FIG. 3, the even numbered lanes are the results of experiments using material from activated T-cells, and the odd numbered lanes are the results of experiments using material from resting T-cells.

In panel B of FIG. 3, lanes 1 and 2 are results from an experiment using a first anchor primer; lanes 3 and 4 are results of the same experiment using a different primer. In lanes 1 to 4, it is readily apparent that by utilizing the same restriction enzyme, but different anchor primers, one will obtain bands of different proteins.

In panel B of FIG. 3, lanes 5 and 6, and 7 and 8, are results of the same experiments and indicate that with the same cDNA but with different restriction enzymes one will obtain different gel patterns.

In panel B of FIG. 3, lanes 9 and 10 are control lanes in which cDNA was cut with restriction enzymes but no adapter or adapter-ligation took place. Thus, lanes 9 and 10 are clear as would be expected of such controls.

As shown In panel C of FIG. 3, sequences that share a common weight but not a common sequence are resolved. Briefly, this was accomplished by introducing a second restriction enzyme into the reaction mixture after ligation and before amplification by PCR. This will not, statistically, cut strands at the same point in both species of cDNA. Thus, statistically the 3'-end obtained in both species will have different numbers of nucleotides. As described above, when subjected to PCR amplification, only the 3'-end will be amplified (because the 5'-ends will not contain the primer; see FIG. 1, steps 5 and 6). Specifically, in panel C, the material in lanes 1 and 2 was cut utilizing Bglll as the restriction enzyme; the material in lanes 3 and 4 were cut utilizing a second restriction enzyme, HinF1.

The bands seen on the gel for experiments utilizing different restriction enzymes can, as described above, be used to determine the different genes that are up- or down-regulated. For example, the band identified as JkA5 in panel C is present in all lanes indicating that the gene is expressed in all tested preparations of active or resting cells. The band identified as JkA6 is present in lane 4 but not lane 3 indicating that this gene is expressed in activated cells, but is not expressed in resting cells; thus providing a means of determining the state of the cell. The band identified as JkA7 is the same in lanes 1, 2 and 4, but is not present in lane 3; again a means is provided for distinguishing between the state of cells based upon the restriction enzyme used. The band identified as JkA7 is present in lanes 1 and 3, the resting cells, but not in the activated cells which provides a means for determining the status of the cell under examination.

Therefore, panel A shows that reproducible patterns were observed on display of Bglll digested cDNAs prepared by using oligo-dT primer RP 6.0 from untreated (lanes 1, 2) and activated (lanes 3, 4) Jurkat RNA samples isolated in two separate experiments. Panel B shows lanes 1, 3, 5, 7 and 9 as representing cDNA samples from untreated, and lanes 2, 4, 6, 8 and 10 from activated, Jurkat cells. Although digested with the same restriction enzyme (Bglll), different cDNAs made from one RNA sample using oligo-dT primers with different anchor bases produce different display patterns (RP9.2 in lanes 1 and 2 and RP 6.0 in lanes 3 and 4). When digested with different restriction enzymes (Bglll in lanes 3 and 4 and BamH1 in lanes 5 and 6) cDNA made from one oligo-dT primer RP6.0 produces different display patterns. Reproducible display patterns were observed between lanes 5 and 6 and 7 and 8 when each cDNA sample of untreated (lanes 5, 7) and activated (lanes 6, 8) Jurkat cells were digested with BamH1 in separate tubes and ligated separately before PCR amplification. When aliquots of restriction enzyme digested cDNAs were separately ligated to the adapter at different times identical patterns were observed on PCR amplification. Lanes 9 and 10 represent unligated controls wherein restriction enzyme digested cDNA is utilized for PCR without ligating the adapter. However, bands may appear in these control lanes if there is a contamination of solutions or samples with adapter ligated cDNA. All samples in panels A and B were run on the same gel, however, lanes 1-4 in panel A, 1 and 2 and 3–10 in panel B were run in adjacent lanes on the gel. With regard to panel C, lanes 1 and 3 represent untreated, and lanes 2 and 4 represent activated, Jurkat cDNAs prepared by using oligo-dt primer RP6.0. In lanes 1 and 2, the cDNA was digested with Bglll, while in lanes 3 and 4 Bglll digested and adapter ligated cDNA was redigested with a more frequent cutting restriction enzyme, HinF1, before PCR amplification. Arrows point to the bands that were extracted and found to be true differences. JkA6 and JkA7 in lane 4 were revealed as differences on the display gel only upon recutting the Bgl II digested cDNA from lanes 1 and 2 with HinF1 before PCR amplification.

Initially, 3' cDNA fragments produced by restriction enzymes Bglll, Bcl1, and BamH1 were displayed in the making of the present invention, as they produce GATC (SEQ. No. 9) overhangs compatible with the same adapter. These enzymes produced different display patterns with the same pool of cDNAs (see FIG. 3, panel B,). Moreover these patterns were consistently reproducible in several different sets of experimental conditions as described above. The reproducibility of the method was also illustrated by the large number of common bands between untreated and activated Jurkat cDNAs (see FIGS. 2 and 3).

To examine the validity of the method, bands were subcloned, sequenced, and specific pair of oligonucleotide primers based on these sequences were used for RT-PCR [see J. Exp. Med. 174:1259 (1991)] with total RNA from untreated and activated normal T cells and Jurkat cells. Two differences in Bglll digested cDNA (FIG. 3, Panel C, lanes 1 and 2) were verified.

Overlapping bands that mask the true differences can be resolved according to the present invention on recutting the adapter ligated 3'-end cDNA fragments (shown in step 5 of FIG. 1) before PCR amplification. If a site for restriction enzyme used for recutting is present in one of the two comigrating bands it will be cut into one part with the adapter and the other with the heel sequence, neither of which can be amplified by PCR, and will therefore, be eliminated. Using this approach, additional differences between untreated and 4 hour activated Jurkat cells were successfully uncovered when Bgl II cut and adapter ligated cDNA were further digested with Hinf1 (FIG. 3, Panel C, lanes 3 and 4).

Any enzyme or enzymes may be used for primary or secondary cutting and a combination of more than one enzymes can be used for recutting. Another advantage of recutting is that recovery of low abundance cDNAs is enhanced because removal of high abundance bands by recutting allows access of these fragments to PCR primers (FIG. 3, panel C, lanes 3 and 4). In addition, recutting can be used to minimize redundancy between fragments in different lanes. For example, Bglll cut cDNA fragments can be recut with BamH1 and vice versa, so that the two samples share no amplified products. A large number of variations of the display patterns can, therefore, be produced by the method according to the present invention to look for differentially expressed genes by (i) a combination of a number of different two base anchored, heeled oligo dT for making cDNAs, (ii) a number of different restriction enzyme that can be used for primary cutting of these cDNAs and, (iii) the number of restriction enzymes used for secondary cutting for each primary cut.

Figure 4:
FIG. 4 is a photomicrograph demonstrating a verification of differences from display gel by RT-PCR of original total RNA sample according to the present invention.
Figure 4:
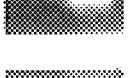
Figure 4:
Figure 4:
Figure 4:
Figure 4:
Figure 4:
Figure 4:
Figure 4:
Figure 4:
Figure 4:
Figure 4:
Figure 4:
Figure 4:
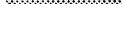
Figure 4:
Figure 4:

Consistent with the reproducibility of the gel patterns, most differences in the intensity of cDNA amplification products corresponded to differences in mRNA levels. For example, a total of 15 bands were subcloned, sequenced and examined by RT-PCR. Of these bands, fourteen showed changes in levels of expression predicted from the gel pattern (FIG. 4, in which the left lane represents material from resting cells, and the right lane represents material from active cells, in addition, sequence 7 represents a band from a normal T-cell, and sequence 7A represents a band from a cancerous T-cell). Of the fourteen sequences, one was myc, one IL-2 and the remainder were novel sequences not represented in conventional sequence databases. Each product contained a polyadenylation signal upstream of the oligo-dT tract. At the other end of each product, the expected four base overhang of the adapter was seen, followed by the base predicted from the specificity of the enzyme used for the initial cutting of the cDNA. For example, bands from display patterns generated with the enzyme Bgl II all had the sequence of the adapter including the GATC (SEQ. NO. 9) of the adapter overhang, followed by a T that would be expected if the 5' end of the attached cDNA had been generated by Bgl II. In every instance, bands recovered from the gel lacked internal cleavage sites for the restriction enzymes used for primary or secondary cutting. The levels of PCR products of the twelve induced and one down-regulated cDNAs, and presumably their mRNAs, vary with respect to the levels of IL-2 and β-Actin (FIG. 4). Therefore, while it is easier to detect and isolate cDNA fragments corresponding to the more abundant mRNAs, the approach according to the present invention provides the ability to detect and subclone samples from quite rare mRNAs.

More specifically with regard to FIG. 4, verification of differences from display gel by RT-PCR of original total RNA sample is shown. In each of the panels 1–15, the left lane represents untreated while the right lane represent activated Jurkat cDNA (In panel 7, however, peripheral blood T-cell RNA was used for RT-PCR). Bands of interest were extracted from the display gel, subcloned, sequenced, and specific PCR primers were made. The method to prepare RNA and RT-PCR has been described [see J. Exp. Med. 174:1259 (1991)]. Briefly, 1 µg of total RNA was reverse transcribed using 100 ng of random hexamer primer in a total volume of 20 µl. Following heat inactivation of reverse transcriptase, the final volume of the reaction mix was adjusted to 50 µl with water, 2 µl of this diluted sample was taken in the final PCR reaction mixture containing 5 µl of 10×PCR buffer (100 mM Tris.HCl and 500 mM KCl), 200 nM of each of the 5' and 3' primers, 200 µM dNTPs, 1 unit of Amplitaq and 1.5 mM $MgCl_2$. PCR consisted of 30 cycles of 94° C. for 30 seconds 55° C. for 1 minute and 72° C. for 30 seconds. PCR samples were analyzed on 1.5% agarose gel and stained with ethidium bromide. Samples in panels 1–15 were analyzed separately, however, IL-2 and β-Actin always showed the same patterns in each experiment as seen in panels 14 and 15, respectively.

Figure 5:
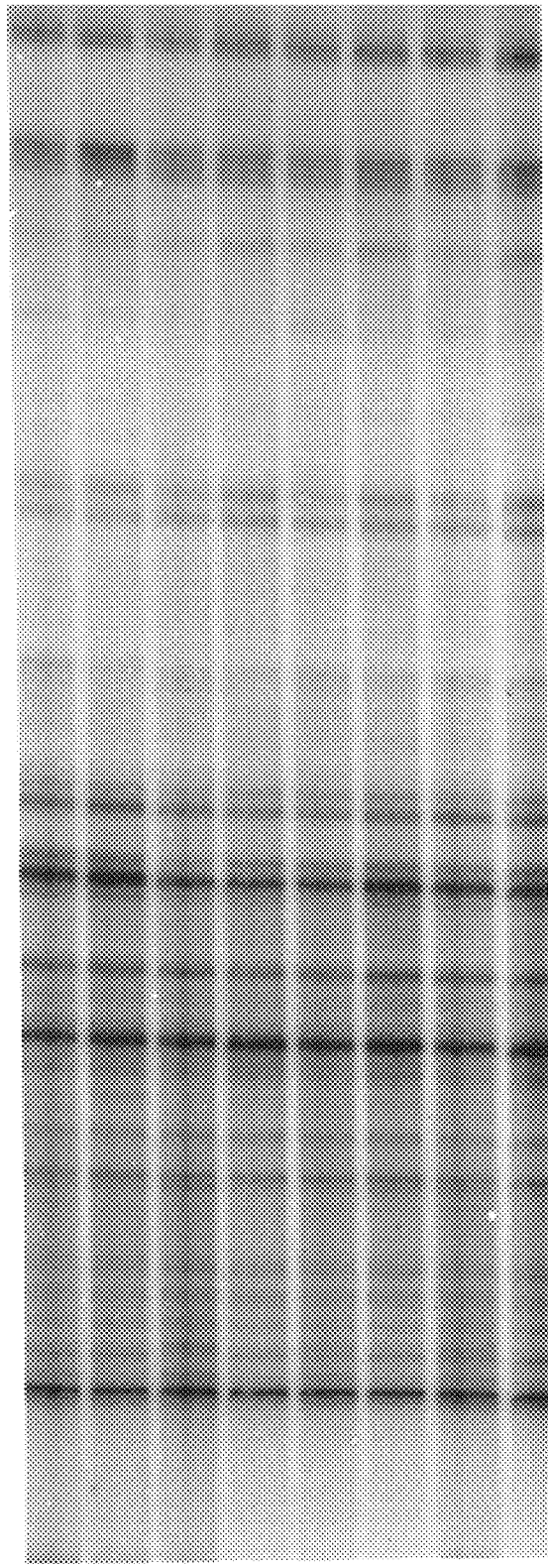
FIG. 5 is a photomicrograph showing utility when using a low amount of cDNA for display according to the present invention.

One advantage of the present invention, as depicted in FIG. 5, is that lower amounts of cDNA, lower than normally required in display protocols, will provide very satisfactory results when used with the protocols described in the present invention. The data depicted as shown in FIG. 5 was derived from a series of experiments to study the effect of using a cDNA concentration about one-fourth the amount of cDNA that is normally required in display protocols. This provides a means for successfully conducting a display study using a smaller-than-presently-required amount of cells from which to obtain the sample material; this application will help to extend the present invention to display of the cDNAs obtained for 10 µg of total RNA to 30 restriction enzymes, in other words, using the present invention 30 different restriction enzymes may be used to successfully display the cDNA prepared from 10 µg of total RNA. Lanes 1 and 2 in FIG. 5 show the display patterns when a normal amount of cDNA is taken (i.e., the amount called for in present display protocols) and subjected to the protocol according to the present invention; lanes 3 and 4 show the display patterns when ¼th of the amount of cDNA that was used in lanes 1 and 2 was restriction enzyme digested, ligated to the Y-shaped adaptor but diluted ¼th less than the dilution used in lanes 1 and 2 after ligation in order to obtain the equivalent concentration of the cDNA as when a normal amount of cDNA is taken as in lanes 1 and 2; lanes 5 and 6 show the display patterns of cDNA which was digested as for the samples run in lanes 1 and 2, but only ¼th of the cDNA was taken for ligation and displayed; and lanes 7 and 8 show the display when ¼th the amount of ligated cDNA that was used in lanes 1 and 2 was taken for PCR amplification. The results clearly show that display patterns identical to those obtained with amounts of cDNA called for by present protocols are obtained even with a low quantities of cDNA. Thus, the present invention may be used with smaller cDNA sample amounts than required in conventional techniques.

Figure 6:
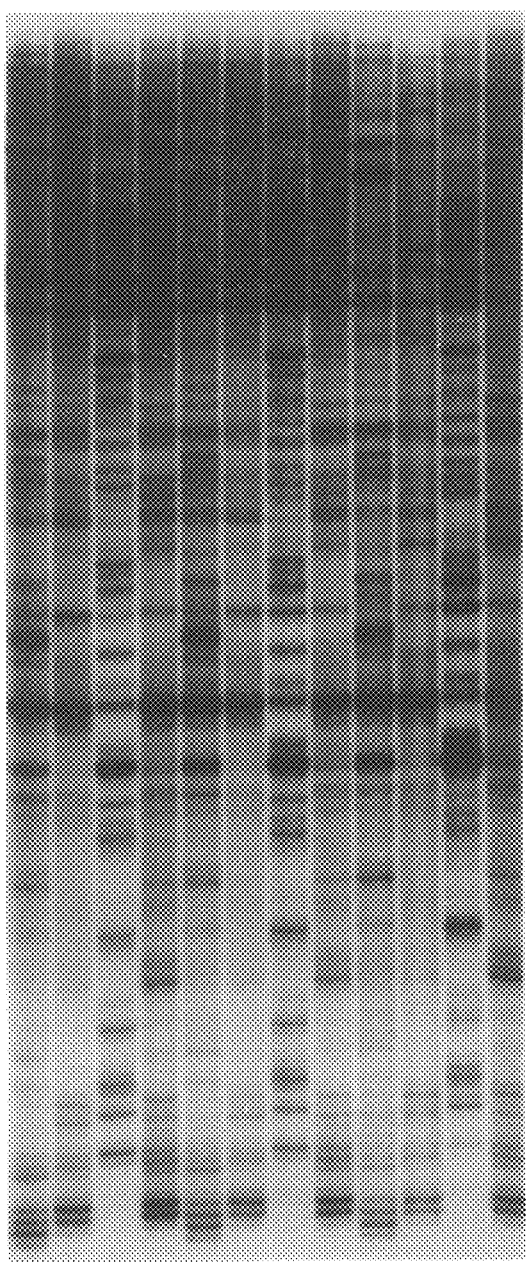
FIG. 6 is a photomicrograph showing the display obtained from cDNA expression patterns in a very small number of stem cells according to the present invention.

Regarding FIG. 6, there is shown a display pattern of cDNA obtained from a very small number of sample cells. More specifically, the figure shows comparisons of the cDNA expression pattern in stem cells at different stages of maturation. In obtaining this data, total RNA was extracted from 5000 stem cells. Using oligo-dT primer, a double stranded cDNA was synthesized, polished, and ligated to an adapter in accordance with the present invention. Using the adapter primers, the cDNA was PCR amplified using the protocol of Baskaran and Weissman [see Genome Research 6(7): 633 (1996)], the disclosure of which is incorporated in toto herein. The original cDNA was therefore amplified several fold so that a large quantity of this cDNA was available for use in the display protocol according to the present invention. For the display, an aliquot of this cDNA was incubated with the anchored oligo-dT primer. This mixture was first heat denatured and then allowed to remain at 50° C. for 5 minutes to allow the anchor nucleotides of the oligo-dT primers to anneal. This provides for the synthesis of cDNA utilizing a klenow DNA polymerase. The 3'-end region of the parent cDNA (mainly the polyA region) that remains single stranded due to pairing and subsequent synthesis of cDNA by the anchored oligo-dT primer at the beginning of the polyA region, is removed by the 5'–3' exonuclease activity of the T4 DNA polymerase. Following incubation of the cDNA with T4 DNA polymerase for this purpose, dNTPs were added in the reaction mixture so that the T4 DNA polymerase would initiate synthesis of the DNA over the anchored oligo-dT primer carrying the heel. The net result of this protocol is that the cDNA with the 3' heel is synthesized for display from the double stranded cDNA as the starting material, rather than RNA as the starting material as occurs in conventional 3'-end cDNA display protocol. The cDNA carrying the 3'-end heel is then subjected to restriction enzyme digestion, ligation, and PCR amplification followed by running the PCR amplified 3'-end restriction fragments with the Y-shaped adapter on the display gel.

Figure 7:
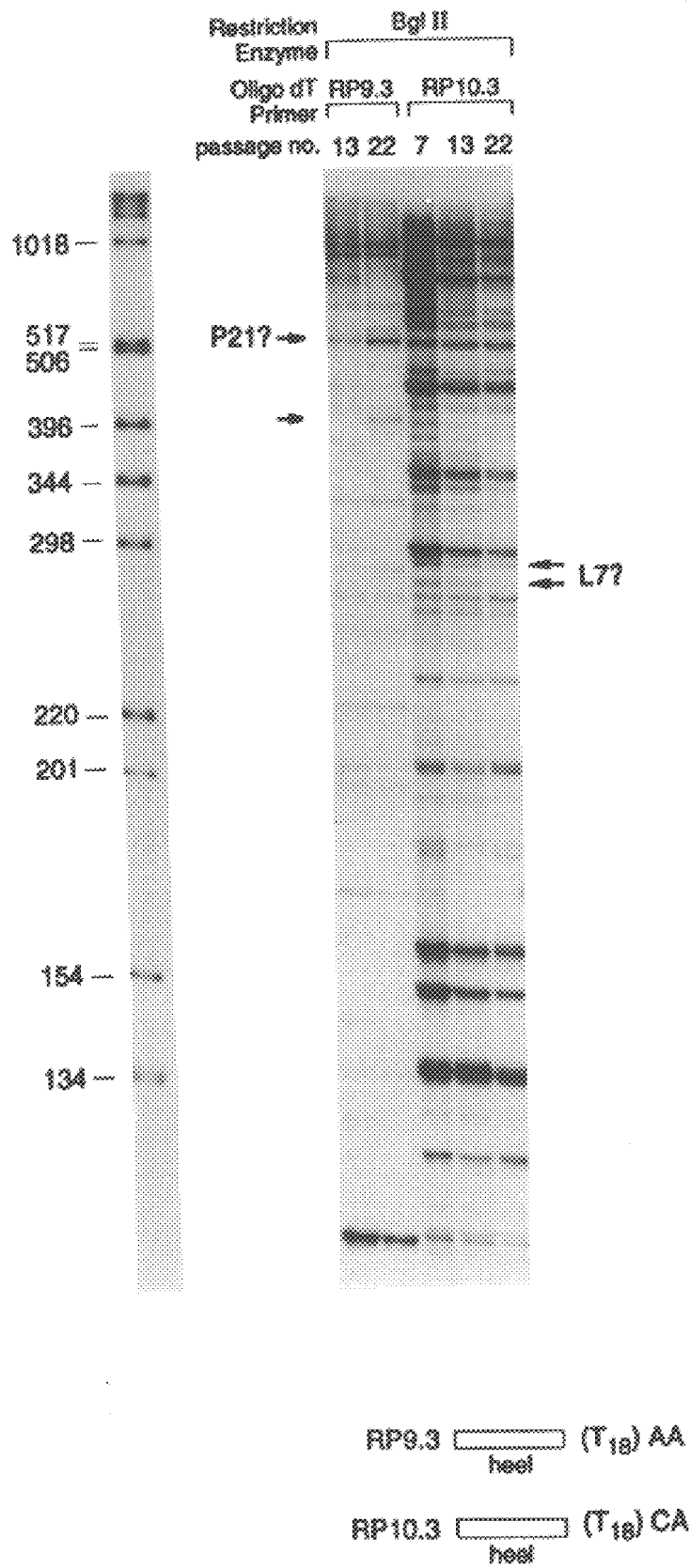
FIG. 7 is a photomicrograph showing the changes in gene expression patterns found in aging IMR 90 cells and using restriction enzyme Bglll according to the present invention.

In FIG. 7 there is shown the display changes which occur in the gene expression patterns of the aging human IMR 90 fibroblast cell line. In order to achieve the results depicted in FIG. 7, the human fibroblast cell line IMR 90 was grown through passages 7, 13 and 22, after which the cells were harvested and total RNA was isolated as described above. These RNA samples were then used for the display protocol according to the present invention. The cDNA that were synthesized following this protocol were digested with the restriction enzyme Bgl II, and run on display gels that are shown in the figure. The arrows on the display pattern depicted in FIG. 7 shows the position of the 3'-end Bgl II fragment of P21 and L7 cDNAs that are known to change during aging.

The sequence (SEQ. NO 13) for RP9.3 is:
CAGGGTAGAC GACGCTACGC TTTTTTTTTT TTTTTTTAA 40.

The sequence (SEQ. NO. 14) for RP10.3 is:
TGGTGGATGG CGTTCCAGGG TTTTTTTTTT TTTTTTTCA 40.

Both heel sequences were selected from the viral DNA sequence so that the PCR primers based on the heel sequence do not amplify any human DNA.

Figure 9:
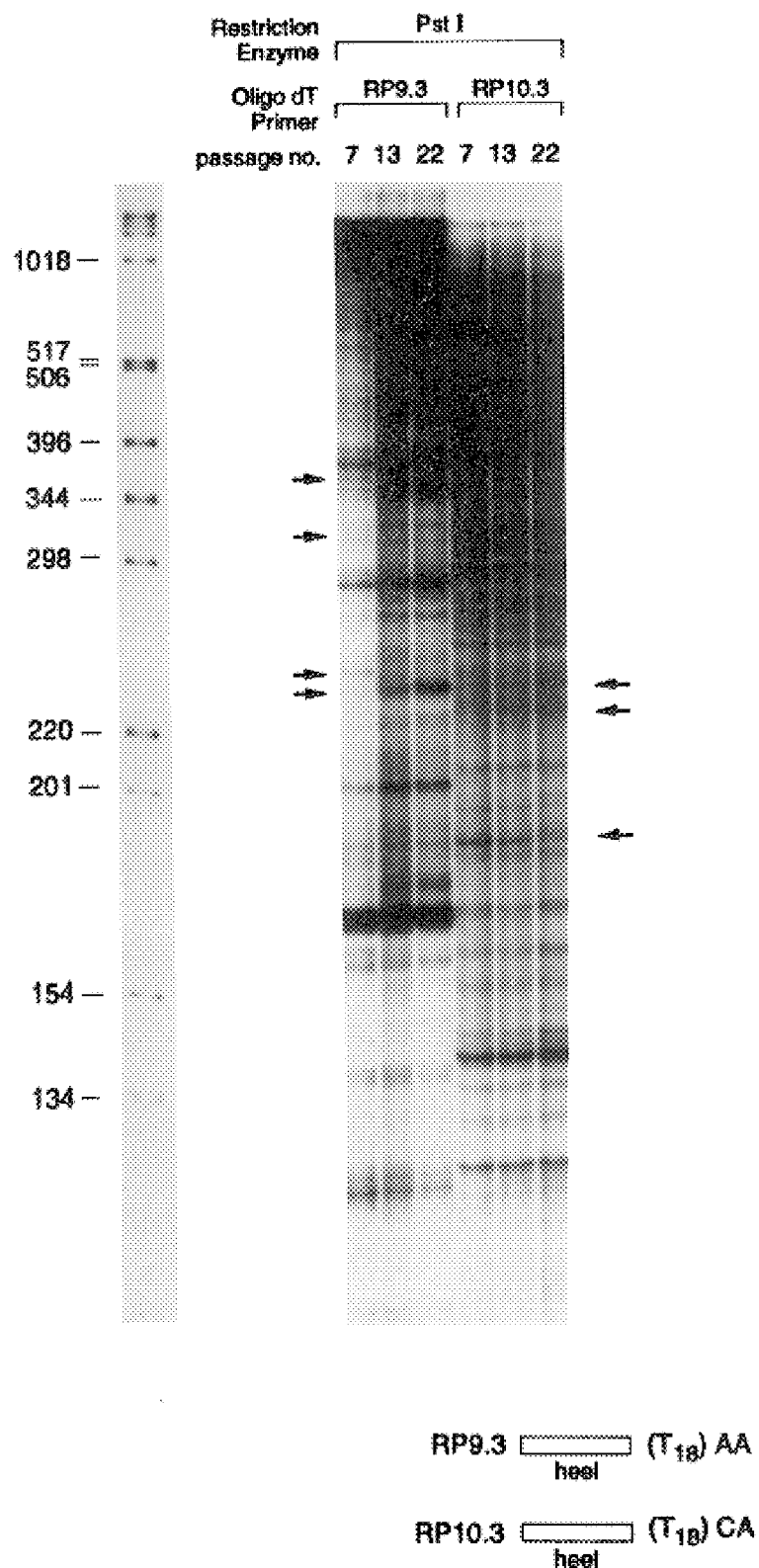
FIG. 9 is a photomicrograph showing the changes in gene expression patterns found in aging IMR 90 cells and using restriction enzyme PStl according to the present invention.

FIG. 9 is similar to FIG. 7 with the exception that the gel depicted in the figure was run with a cDNA that was digested with the restriction enzyme Pst I. In this case, the arrows show the position of bands in the display pattern that change during aging. Both FIGS. 7 and 9 thus support the use of the present invention for studies involving the changes which occur in gene expression during the maturation or aging of cells.

Figure 8:
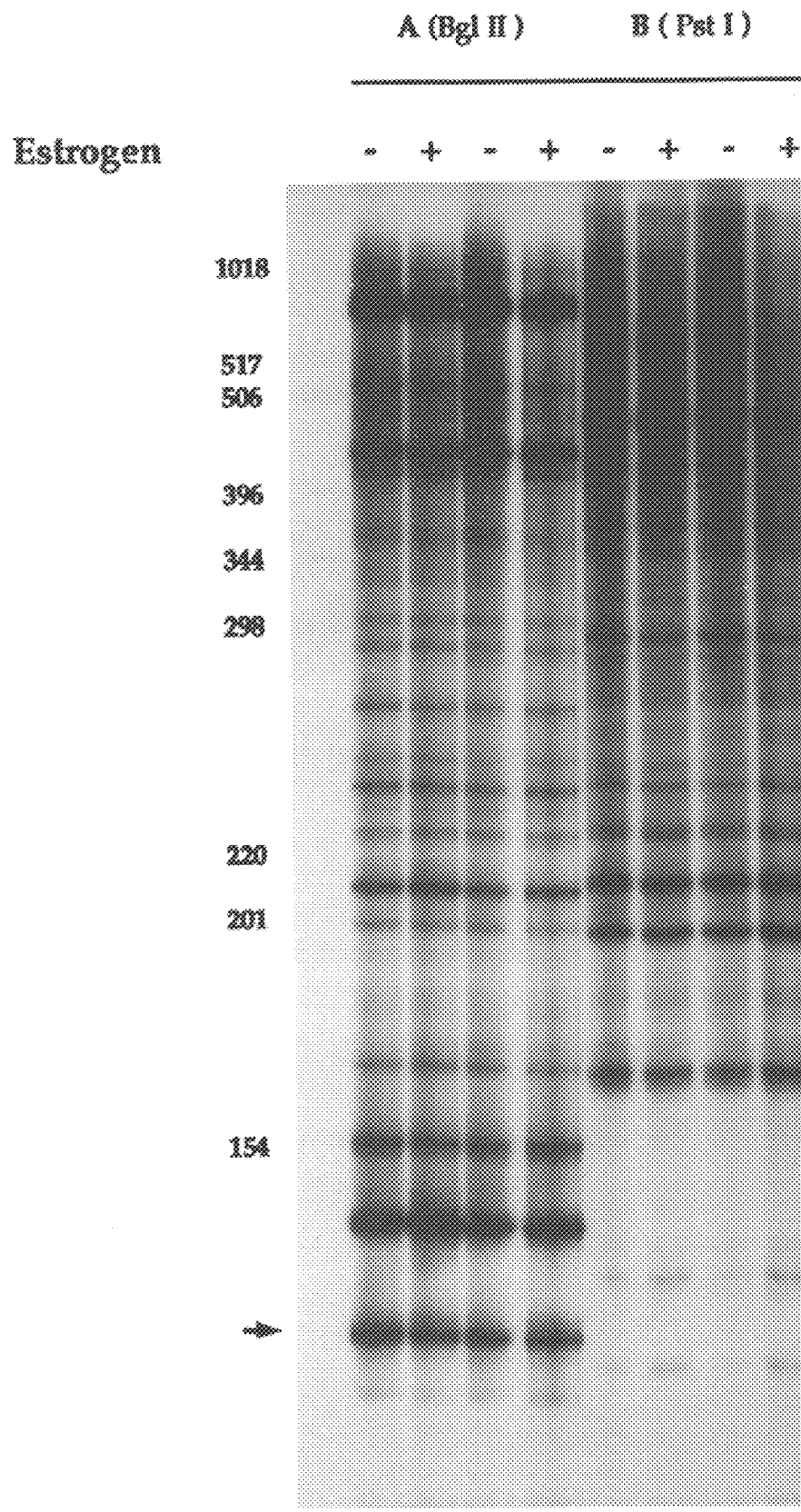
FIG. 8 is a photomicrograph showing the display obtained of cDNA expression patterns from human osteoblasts treated with and without estrogen according to the present invention.

FIG. 8 depicts the gene expression changes that occur in cells exposed to exogenous molecules such as the hormone estrogen. In FIG. 8, osteoblasts form a 17 year old female patient were obtained from spinal bone chips by allowing cells to grow out of the chips onto plastic culture dishes after which the cells were passaged twice and allowed to grow to confluence in the dishes. After 48 hours in the absence of estrogen, 10 mN 17-β-estradiol was added to the cell culture. Control cells remained in estrogen-free media. 24 hours later, RNA was isolated and analyzed according to the display protocol of the present invention. cDNA was prepared from control RNA(−) or estrogen treated RNA(+) cells which were digested with Bgl II or Pst I restriction enzymes and run on the display gel as described above. As indicated by the arrow in the figure, this protocol results in a gel that shows the position of one band which is present in the treated cells (i.e., RNA(+)), but absent in the control cells. Thus, the protocol of the present invention may also be used to distinguish the effect that an exogenous molecule may have upon various cell types.

Figure 10:
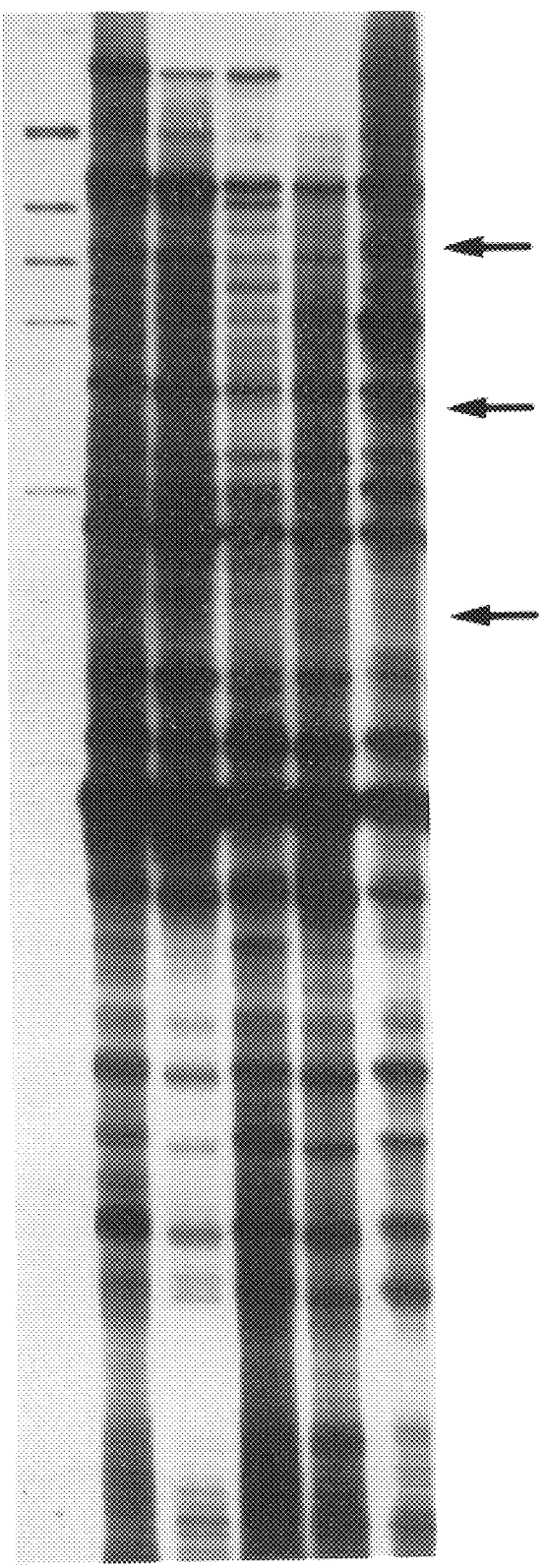
FIG. 10 is a photomicrograph showing the display of cDNA expression patterns of Jurkat T-cells after transfection with the HOX11 gene according to the present invention.

The display of cDNA expression pattern of Jurkat T-cells after transfection with the HOX11 gene is shown in FIG. 10. It is known that the overexpression of the HOX11 gene in T-cells results in leukemia [see *Blood* (Suppl.) 80:355a (1992)]. In order to study which cDNAs might be induced in T-cells as a result of HOX11 overexpression, the cDNA for HOX11 was transfected into Jurkat cells according to standardized protocol in a tet expression vector [see *Proc. Natl. Acad. Sci. USA* 92:6522 (1995), for example], and the cDNA expression patterns between non-transfected and HOX11 transfected Jurkat T-cells were compared on display gels prepared as described above. As depicted in FIG. 10, lane 1 contained a 1 kb marker; 2 contained cDNA samples taken from Jurkat T-cells transfected with the vector plasmid ptet-tak (tak is the plasmid vector that contains the tet-VPIG fusion gene used for transactivation and under tet control; a control); lane 3 contained cDNA samples taken from Jurkat T-cells transfected with the vector plasmid ptet-splice (a control); lane 4 contained cDNA samples taken from Jurkat T-cells transfected with the vector plasmid ptet-HOX11 (a control); lane 6 contained cDNA samples taken from Jurkat T-cells transfected with the vector plasmid ptet-tak+ptet-HOX11, i.e., a mixture of both plasmids, taken at 0 hours after transfection; and lane 6 contained cDNA samples taken from Jurkat T-cells transfected with the vector plasmid ptet-tak+ptet-HOX11 taken 1 hour after transfection. The arrows in FIG. 10 indicate some of the cDNA bands that are induced as a result of HOX11 cDNA overexpression, and again support the use of the present invention as a means to locate and identify the initiation of gene expression in cells which have undergone a change from a resting, stable and normal state of existence.

One of the most important factors affecting clarity of the display patterns is the quantity of template for PCR and the number of PCR cycles. We found ~100 pg of cDNA template is appropriate for PCR amplification. However, before attempting to analyze differences in display gels, we routinely PCR amplified serial dilutions of the template to choose a concentration that would produce clear and reproducible patterns in 28–30 PCR cycles. High template concentrations produced smeary patterns while at very low template concentration bands started to drop out, producing artefactual differences on the gel. Good quality of RNA is also a prerequisite for clean display patterns. Replicates of PCR amplified samples were run on the gel to look for the consistency in the difference of intensity of the band under consideration and unligated cDNAs were PCR amplified as controls that showed bands only if there was contamination of adapter ligated cDNA in solutions or sample. We found subcloning a band of interest better than direct analysis of the reamplified band recovered from the gel and it is necessary to examine that recovered band is of the correct size.

Increasing the number of 3' cDNA end fragments in a sample can cause blurred patterns. Sau3A1 (a four base cutter) produced smeary patterns although the same amount of cDNA digested with Bglll or BamH1 (six base cutters) produced clear gel patterns. Sau3A1 is a frequent cutter and produces more amplifiable 3'-ends from a cDNA population which then crowd together on the gel. RNA primed with oligo-dT primers containing a mixture of bases in the subterminal anchor position produced crowded patterns because a larger number of cDNA molecules were synthesized.

The extent to which anchored oligo-dT primers prime cDNA synthesis from mRNAs whose sequence does not match the anchor bases perfectly has been a major limitation of cDNA display methods. In the present invention a number of conditions to enhance specificity of this priming were examined, and it was found that primer extension by reverse transcriptase at 50° C. was optimal. However, even under these optimized conditions some known cDNA products arose because of mispairing or looping out of the subterminal anchor base. Nevertheless, different yet consistent and reproducible patterns were obtained with cDNAs made from oligo-dT primers with different anchor bases.

Overall, from four pairs of lanes representing untreated and activated Jurkat cell mRNAs, about 700 bands could be evaluated. Of these, about 4% appeared to represent species that increase (up-regulated) on activation and as many as 2% significantly decreased (down-regulated) on activation. T-cell activation is an extensively studied phenomenon and about 80 genes whose expression is increased in the early phase of activation have been recognized [see Annul. Rev. Immunol. 8:421 (1990)]. In the present experiments, the estimated number of 3'-end mRNA sequences whose expression is altered within four hours after T-cell activation is an order of magnitude higher than might be presumed from earlier studies [see Proc. Natl. Acad. Sci. 84:1609 (1987); Nature 308:149 (1984); and Mol. Cell Biol. 9:1041 (1989)]. However, one limitation common to all methods of 3'-end cDNA display is that apparent differences in expression may arise if sites of polyadenylation of a single species of mRNA changed after activation.

One cDNA, JkR1, that was down-regulated on activation in both peripheral blood T-cells and Jurkat cells was chosen for further study. Down-regulation of JkR1 in peripheral blood T-cells was evident 4 hours after activation with the addition of ionomycin and diacylglycerol. When resting T-cells were exposed to actinomycin D, JkR1 mRNA was relatively stable for up to 3 hours. This raises the possibility that part of the down-regulation might be activated by mRNA destabilization. Phillipson has studied a small group of GAS genes whose mRNA declines on refeeding cells with serum [see Cell 54:787 (1988)], and several of these mRNAs were also down-regulated by destabilization [see Mol. Cell Biol. 6:2924 (1990)]. However, JKR1 is different from the GAS genes both in sequence and in the fact that the level of its mRNA was not depressed simply by refeeding but only after specific activation of T-cells.

Strikingly, there are very few references in the literature to genes whose expression is down regulated on T-cell activation [see Nucleic Acids Res. 19:4655 (1991); and Proc. Natl. Acad. Sci. USA 90:10260 (1993)]. This suggests that changes in the intracellular environment upon T-cell activation is a combined result of down-regulation of a set of genes in addition to induction of gene expression.

The method of the present invention has shown the ability to uncover multiple differences between rather similar samples of untreated and 4 hr activated Jurkat T-Cells. The reproducibility and extensive representation obtained with this method allows a systematic analysis of a sample, taking full advantage of sequence databases. Since the lane and size of the band of a known gene can be easily predicted, gel patterns can be used to evaluate changes in the level of expression of known mRNAs without resorting to cloning or further analysis. As a large fraction of cDNAs become represented in the databases as 3' ESTs, one can use data base searches to limit or define candidate genes corresponding to any band whose abundance changes. This will be an increasingly powerful approach as more cDNA and genomic sequences accumulate. Furthermore, by using fluorescent primers, automated analysis of the control and test samples can be carried out in a single lane. And finally, the use of two different restriction sites, one for the adapter and the other for the heel primer can expedite and orient the cloning. Because of its sensitivity, this approach could be used to study the time course of appearance or disappearance of a set of mRNAs in a variety of eukaryotic systems and extrapolate back to shorter time intervals after the initiating stimulus is applied.

In summary, the present invention provides an approach to study changes in gene expression by selective PCR amplification and display of 3'-end restriction fragments of double stranded cDNAs. The method according to the present invention produces highly consistent and reproducible patterns, can detect almost all mRNAs in a sample, and can resolve hidden differences such as bands that differ in their sequence but comigrate on the gel. Bands corresponding to known cDNAs move to predictable positions on the gel, making this a powerful approach to correlate gel patterns with cDNA databases. Applying the method according to the present invention, we have examined differences in gene expression patterns during T-cell activation. Of a total of 700 bands that were evaluated in the T-cell activation studies during the making of the present invention and described herein, as many as 3–4% represented mRNAs that are up-regulated, while about 2% were down-regulated within 4 hours of activation of Jurkat T-cells. These results suggest that the method according to the present invention is suitable for the systemic, expeditious and nearly exhaustive elucidation of subtle changes in the patterns of gene expression in cells with altered physiologic states.

Thus while we have illustrated and described the preferred embodiment of our invention, it is to be understood that this invention is capable of variation and modification and we therefore do not wish to be limited to the precise terms set forth, but desire to avail ourselves of such changes and alterations which may be made for adapting the invention to various usages and conditions. For example, while the gels prepared and shown in the figures are prepared according to conventional gel technology, the fragments run in these gels may be alternatively labelled with fluorescent labels and the reading of the gels conducted by automated means. Also, while specific sized oligonucleotide primers are depicted in the embodiments described herein, the exact length and nucleotide sequence of these primers may be varied while still maintaining the requirements that these primers must have as described herein. Also, while the embodiment described herein is directed primarily at the assay of changes occurring in activated and resting cells, it is to be understood that whenever a cell is brought into contact with an exogenous material such as for example a pharmaceutical or toxic compound, the cell will invariably provide some genetic response to the material resulting in the up- or down-regulation of genetic expression; these changes can also be noted using the method according to the present invention with very little alteration to the general scheme of the method depicted in FIG. 1, and these changes can be used to evaluate the effect that such materials have on the host cell that has been exposed to the material.

In addition to the above, other applications of the 3'-end cDNA differential display protocols according the present invention would include the elucidation of the mechanism of drug action (with the ability to monitor early changes in the cell after drug treatment, the mechanism of drug action can be studied by applying the 3'-end cDNA techniques described herein, also a comparison of responses of different individuals to a drug treatment can be monitored); comparison of early side effects at the molecular level in response to the treatment with different drugs for a common cure (certain drugs are known to have more side effects or toxicity than others that are used to treat the same disorder, and the display techniques described herein will be useful in the rapid evaluation of different drug therapies for their side effects); and the ability to display differences in target cells that are scarce in number (this use will be especially helpful in cases where stem cells are being studied, or in the case of biopsies where only a small amount of tissue is available). Still in addition to the above, it will also be possible by a variation of the present invention as described above to display both the 5'-end of a nucleic acid sequence, as well as internal cDNA fragments which, along with the 3-end display, as fully described herein, will allow for the detection of, for example, mutations in normal and hereditary disorders. What makes the present invention applicable to each of these possible uses is that they all result in subtle changes in gene expression for which the present invention provides a means to study and note such changes.

Accordingly, such changes, modifications, alterations and uses as described herein or as would be readily apparent to those skilled in the art are properly intended to be within the full range of equivalents, and therefore within the purview of the following claims.

A complete listing of all nucleotide sequences described in the above description of the present invention follows.

Having thus described our invention and the manner and process of making and using it in such full, clear, concise, and exact terms so as to enable any person skilled in the art to which it pertains, or with it is most nearly connected, to make and use the same.

We claim:

1. A method for selectively amplifying in a nucleic acid sample a DNA fragment having sequence complementary to a 3' end of an mRNA, comprising the steps of:
   (a) contacting the mRNA with an oligonucleotide primer that hybridizes to a portion of the polyA tail of the mRNA;
   (b) reverse transcribing the mRNA to produce a first strand cDNA;
   (c) synthesizing a second DNA strand complementary to the first strand cDNA to form a first duplex;
   (d) ligating a double stranded adapter to the first duplex;
   (e) amplifying the ligated duplex using a primer that hybridizes to one strand of the double-stranded adapter;
   (f) contacting the amplified duplex with an oligonucleotide primer comprising a 5' sequence incapable of hybridizing to a polyA tail of the cDNA, and a 3' sequence that hybridizes to a portion of the polyA tail of the cDNA and at least one non-polyA nucleotide immediately upstream of the polyA tail;
   (g) transcribing the cDNA to produce a first strand DNA that includes the oligonucleotide primer;
   (h) synthesizing a second DNA strand complementary to the first strand DNA to form a second duplex;
   (i) cleaving the second duplex with at least one sequence-specific cleaving agent to provide a number of duplex cleavage fragments;
   (j) ligating an adapter to the cleavage fragments, the adapter to the cleavage segments consisting of two partially hybridized nucleic acid strands, wherein portions of the two strands are non-complementary to each other and portions of the two strands are complementary to each other; and
   (k) amplifying the ligated cleavage fragments using a first primer whose sequence comprises at least a portion of the 5' sequence of the oligonucleotide primer of step (f) and a second primer whose sequence comprises at least a portion of the sequence of one strand of the adaptor in the non-complementary portion, thereby selectively amplifying a DNA fragment comprising sequence complementary to a 3' end of an mRNA.

2. The method of claim 1, wherein the 5' sequence of the oligonucleotide primer of step (f) comprises a sequence that provides a restriction enzyme site in the duplex of step (h).

3. The method of claim 1, wherein the adapter comprises a first portion, wherein the two strands are noncomplementary to each other and a second portion, wherein the two strands are complementary to each other; resulting in a partially hybridized adapter that is Y-shaped.

4. The method of claim 1, wherein one of the two strands of the noncomplementary portion comprises a sequence that provides a restriction enzyme site in the amplified fragment of step (k).

5. The method of claim 1, wherein the mRNA is isolated from cells or tissue.

6. The method of claim 1, wherein at least one of the primers in step (k) is labeled.

7. The method of claim 6, wherein the label is a fluorescent label.

8. The method of claim 1, further comprising after step (j), reacting at least one sequence-specific cleaving agent with the ligated fragments.

9. The method of claim 1, further comprising after step (k), detecting the amplified fragment.

10. A method for comparing the levels of mRNA expression in two cell populations, comprising:
    selectively amplifying in a nucleic acid sample from each cell population a DNA fragment comprising sequence complementary to a 3' end of an mRNA according to the method of claim 1; and
    comparing the amounts of amplified fragments obtained in step (k) of claim 1.

11. The method of claim 10, wherein at least one of the primers for amplification is labeled.

12. The method of claim 11, wherein the label is a radiolabel or fluorescent label.

13. The method of claim 12, wherein one of the cell populations is treated.

* * * * *

```
                            SEQUENCE LISTING (1) GENERAL INFORMATION:

(iii) NUMBER OF SEQUENCES:  14

(2) INFORMATION FOR SEQ ID NO:1:

(i) SEQUENCE CHARACTERISTICS:
        (A) LENGTH: 6 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:1:

AATAAA                                                                   6

(2) INFORMATION FOR SEQ ID NO:2:

(i) SEQUENCE CHARACTERISTICS:
        (A) LENGTH: 40 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:2:

CTCTCAAGGA TCTTACCGCT TTTTTTTTTT TTTTTTTAT                               40

(2) INFORMATION FOR SEQ ID NO:3:

(i) SEQUENCE CHARACTERISTICS:
        (A) LENGTH: 40 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:3:

TAATACCGCG CCACATAGCA TTTTTTTTTT TTTTTTTCG                               40

(2) INFORMATION FOR SEQ ID NO:4:

(i) SEQUENCE CHARACTERISTICS:
        (A) LENGTH: 40 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:4:

CAGGGTAGAC GACGCTACGC TTTTTTTTTT TTTTTTTGA                               40

(2) INFORMATION FOR SEQ ID NO:5:

(i) SEQUENCE CHARACTERISTICS:
        (A) LENGTH: 25 base pairs
        (B) TYPE:nucleic acid
```

(C) STRANDEDNESS:single
        (D) TOPOLOGY:linear (ii) MOLECULE TYPE:DNA (xi) SEQUENCE DESCRIPTION: SEQ ID NO:5:

TAGCGTCCGG CGCAGCGACG GCCAG    25

(2) INFORMATION FOR SEQ ID NO:6:

(i) SEQUENCE CHARACTERISTICS:
        (A) LENGTH: 29 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:6:

GATCCTGGCC GTCGGCTGTC TGTCGGCGC    29

(2) INFORMATION FOR SEQ ID NO:7:

(i) SEQUENCE CHARACTERISTICS:
        (A) LENGTH: 19 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:7:

TAGCGTCCGG CGCAGCGAC    19

(2) INFORMATION FOR SEQ ID NO:8:

(i) SEQUENCE CHARACTERISTICS:
        (A) LENGTH: 209 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:8:

TAGCGTCCGG CGCAGCGACG GCCAGGATCT TTTATGATTC TTTTTGTAAG    50

CCCTAGGGGC TCTAAAATGG TTTCACTTAT TTATCCCAAA ATATTTATTA    100

TTATGTTGAA TGTTAAATAT AGTATCTATG TAGATTGGTT AGTAAAACTA    150

TTTAATAAAT TTGATAAATA TTTTTTTTTT TTTTTTTTTT CGCCATTCTA    200

GGAACTCTC    209

(2) INFORMATION FOR SEQ ID NO:9:

(i) SEQUENCE CHARACTERISTICS:
        (A) LENGTH: 4 base pairs
        (B) TYPE:nucleic acid
        (C) STRANDEDNESS:single
        (D) TOPOLOGY:linear (ii) MOLECULE TYPE:DNA

```
    (xi) SEQUENCE DESCRIPTION: SEQ ID NO:9:

GATC                                                                         4

(2) INFORMATION FOR SEQ ID NO:10:

(i) SEQUENCE CHARACTERISTICS:
        (A) LENGTH: 20 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:10:

CTCTCAAGGA TCTTACCGCT                                                       20

(2) INFORMATION FOR SEQ ID NO:11:

(i) SEQUENCE CHARACTERISTICS:
        (A) LENGTH: 20 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:11:

TAATACCGCG CCACATAGCA                                                       20

(2) INFORMATION FOR SEQ ID NO:12:

(i) SEQUENCE CHARACTERISTICS:
        (A) LENGTH: 20 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:12:

CAGGGTAGAC GACGCTACGC                                                       20

(2) INFORMATION FOR SEQ ID NO:13:

(i) SEQUENCE CHARACTERISTICS:
        (A) LENGTH: 40 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:13:

CAGGGTAGAC GACGCTACGC TTTTTTTTTT TTTTTTTTAA                                  40.

(2) INFORMATION FOR SEQ ID NO:14:

(i) SEQUENCE CHARACTERISTICS:
        (A) LENGTH: 40 base pairs
        (B) TYPE:nucleic acid
        (C) STRANDEDNESS:single
        (D) TOPOLOGY:linear (ii) MOLECULE TYPE:DNA (xi) SEQUENCE DESCRIPTION: SEQ ID NO:14:

TGGTGGATGG CGTTCCAGGG TTTTTTTTTT TTTTTTTCA                                   40.
```